US00PP34121P2

(12) United States Plant Patent
Tang

(10) Patent No.: US PP34,121 P2
(45) Date of Patent: Apr. 12, 2022

(54) TABLE GRAPEVINE PLANT NAMED 'CXG20'

(50) Latin Name: *Vitis labrusca*
Varietal Denomination: CXG20

(71) Applicant: Zunrong Tang, Bakerfield, CA (US)

(72) Inventor: Zunrong Tang, Bakerfield, CA (US)

(73) Assignee: Cheng Xin Garden llc, Bakersfield, CA (US)

( * ) Notice: Subject to any disclaimer, the term of this patent is extended or adjusted under 35 U.S.C. 154(b) by 0 days.

(21) Appl. No.: 17/201,626

(22) Filed: Mar. 15, 2021

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

*Primary Examiner* — Keith O. Robinson
(74) *Attorney, Agent, or Firm* — Cassandra Bright

(57) ABSTRACT

A new and distinct variety of table grapevine plant named 'CXG20' is herein disclosed. 'CXG20' produces sweet, dark purple fruit with a uniquely strong flavor which is a mixture of muscat and labrusca. Fruits are very juicy and somewhat soft. 'CXG20' is a very early season variety, the fruit commonly is ready for harvesting from the end of June until mid-July in Bakersfield, Calif.

2 Drawing Sheets

Latin name of the genus and species: *Vitis labrusca.*
Variety denomination: 'CXG20'.

BACKGROUND OF THE INVENTION

A breeding program was initiated during 2003 at a research nursery in Bakersfield, Calif. The female parent of the new variety is 'Kyoho', unpatented. The male parent is an unnamed, unpatented variety of *Vitis labrusca*. The crossing resulting in 'CXG20' as made during May of 2015.

'CXG20' was identified as a potentially interesting selection during July of 2017 at a research nursery in Bakersfield, Calif. After identifying the new variety as a potentially interesting selection, first propagation of 'CXG20' by vegetative cuttings was undertaken during 2018, at the research nursery in Bakersfield, Calif. Controlled testing and propagation of the new variety continued, to assess stability of the unique characteristics of this variety. Subsequently, several generations have been reproduced and have shown that the unique features of this cultivar are stable and reproduced true to type. No publications have been issued on the plant breeding invention.

SUMMARY OF THE INVENTION

The cultivar 'CXG20' has not been observed under all possible environmental conditions. The phenotype may vary somewhat with variations in environment such as temperature, day length, and light intensity, without, however, any variance in genotype. The following characteristics in combination distinguish 'CXG20' as a new and distinct *Vitis* cultivar:

1. Strong flavor with a mixture of muscat and labrusca
2. Very fruity aroma, gummy bear flavor
3. Average Sweet Brix range from 23 to 28

4. Very juicy and somewhat soft
5. Vine is drought and heat resistant.

COMPARISON TO PARENT VARIETIES

Plants of the new cultivar 'CXG20' are comparable to the seed parent in most horticultural characteristics; however, the new variety 'CXG20' differs in the following:

1. Fruit of the new variety is firmer than fruit of the seed parent.
2. Fruit of the new variety is smaller than fruit of the seed parent.
3. Fruit of the new variety has a stronger Muscat flavor than fruit of the seed parent.
4. Fruit of the new variety is sweeter, with less acidity than the seed parent.
5. The new variety ripens approximately 3 weeks earlier than the seed parent in the Central Valley of California.

Plants of the new cultivar 'CXG20' are comparable to the pollen parent in most horticultural characteristics; however, the new variety 'CXG20' differs in the following:

1. Fruit of the new variety is firmer than fruit of the pollen parent.
2. Fruit of the new variety has a stronger Muscat flavor than fruit of the pollen parent.
3. Fruit of the new variety is sweeter, with less acidity than the pollen parent.

COMMERCIAL COMPARISON

Plants of the new cultivar 'CXG20' are comparable to the commercial variety 'Sarah Anne', U.S. Plant Pat. No. 14,193 in most horticultural characteristics; however, the new variety 'CXG20' differs in the following:

1. Fruit of the new variety is orbicular; fruit of the comparator is oblong.
2. Flowering of 'Sarah Anne' begins around May 5; flowering of this comparator begins mid to late May.

3. Fruit of the new variety is ready for harvest beginning around the end of June with harvest until about mid-July. Fruit of this comparator is usually ready for harvest around the first week of August.

BRIEF DESCRIPTION OF THE PHOTOGRAPHS

The accompanying photographic illustrations shows typical samples of fruit produced by the new variety. Colors in the photograph may differ from the color values cited in the detailed botanical description below.

DETAILED BOTANICAL DESCRIPTION

Figure 1:
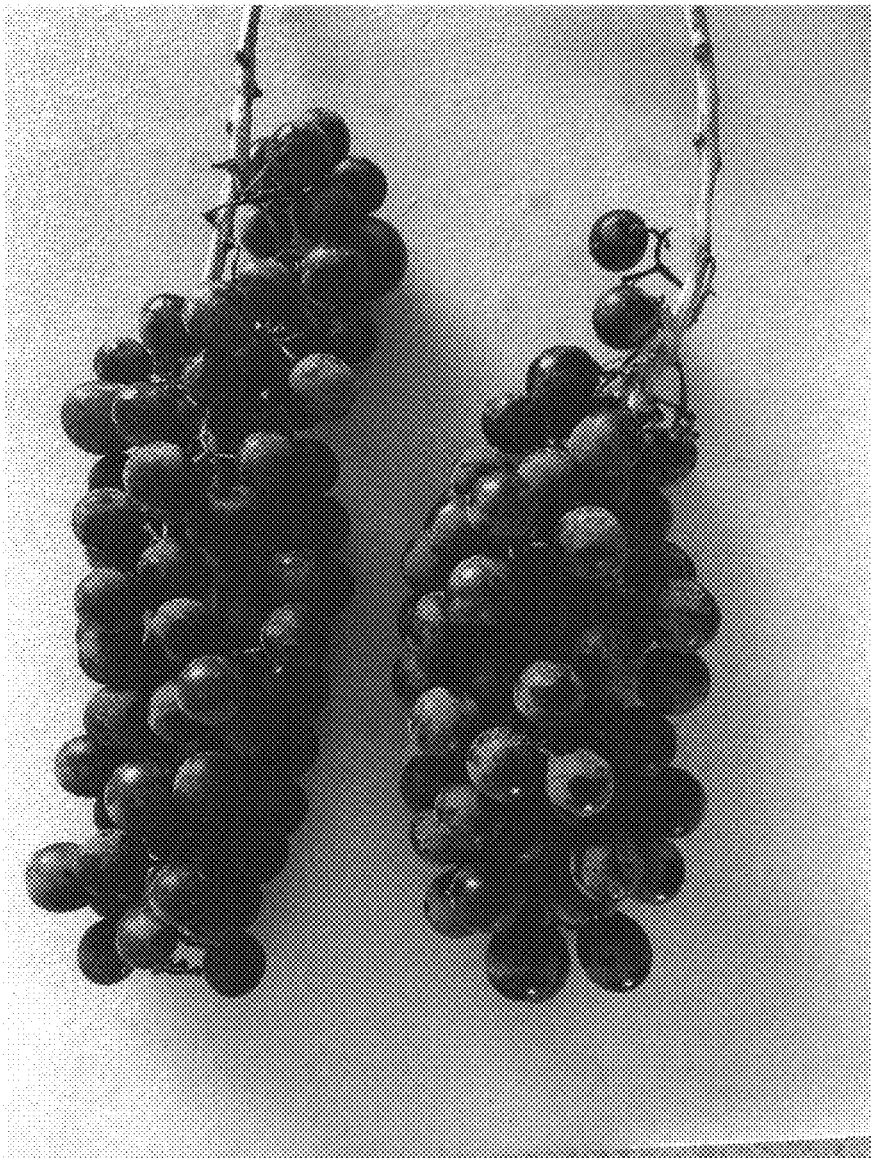
FIG. 1 illustrates two fruit clusters produced by 'CXG20'. The cluster on the left is beginning to ripen, the cluster in the right of the figure is a cluster of fully ripe fruits from 'CXG20.
Figure 2:
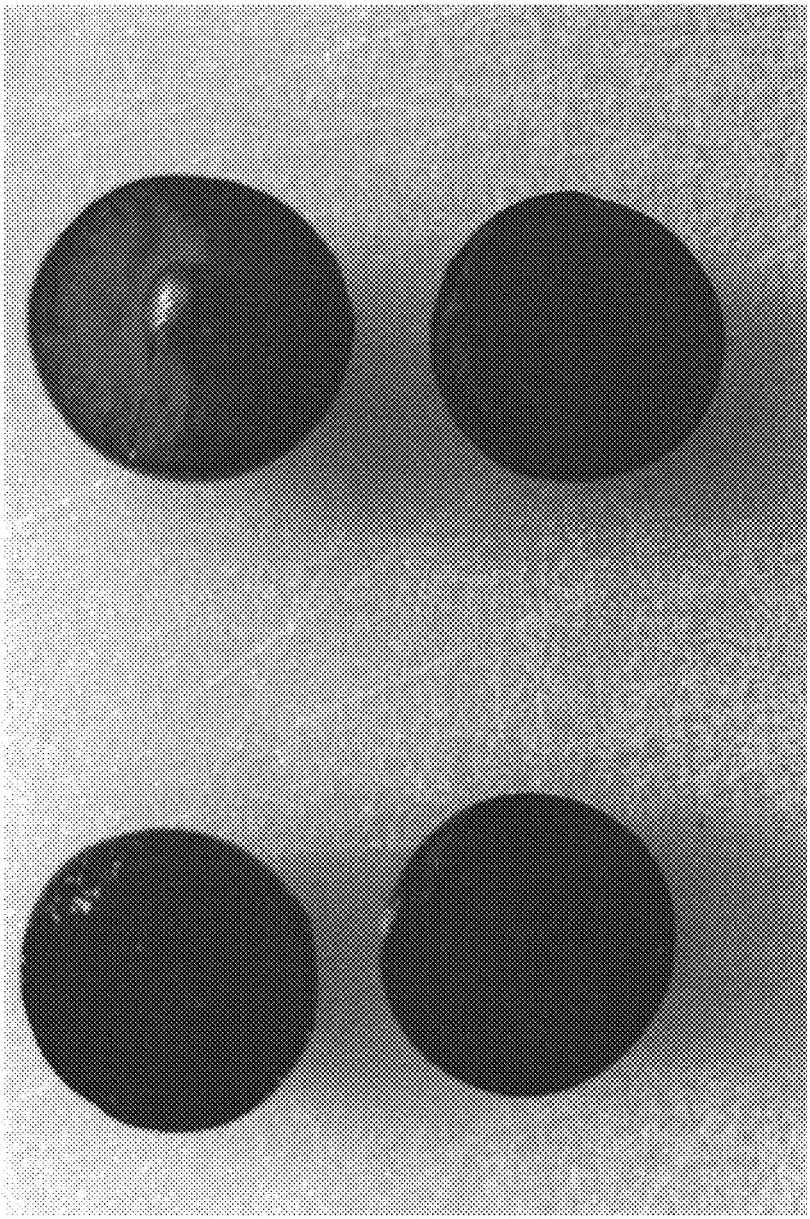
FIG. 2 shows a close-up, cross-section view of the interior of fruits of 'CXG20'. The fruits on the top of the figure are ripening, the fruits on the bottom are fully ripe.

In the following description, color references are made to The Royal Horticultural Society Colour Chart 2007 except where general terms of ordinary dictionary significance are used. Some descriptors, when useful have been incorporated from *UPOV Grape Descriptor Guidelines*. Plants were grown in Bakersfield, Calif. and are approximately 2 years old.

Botanical classification: *Vitis labrusca* 'CXG20'.

CANES

Characteristics of mature canes:

*Form*.—Round with fine ridges.
*Diameter*.—Average range 7 to 10 mm.
*Length*.—1.3 to 2 m.
*Color*.—Near RHS Yellow-Green N144D flushed Greyed-Orange 177A and 177B.
*Cross section shape*.—Round.
*Strength*.—Average.
*Texture*.—
*Lenticels*.—Not observed present.
*Internode length*.—8 to 19 cm. Bud break: Early. Late March, in the central Valley of California.
*Tendrils forked* (*yes/no*).—Yes.
*Tendril texture*.—Glabrous.
*Tendril length*.—7 to 12 cm.
*Openness of the tip of the young shoot*.—Half open.
*Young shoot prostrate hairs*.—Very sparse.

FOLIAGE

Leaf:

*Arrangement*.—Alternate.
*Quantity*.—Approximately 22 per cane.
*Average length*.—15 cm.
*Average width*.—19 cm.
*Internode*.—8-12 cm.
*Overall shape of blade*.—Broad ovate.
*Apex*.—Acute.
*Base*.—Rounded.
*Margin*.—3 lobed, dentate.
*Texture of top surface*.—Smooth.
*Texture of bottom surface*.—Smooth.
*Pubescence*.—None.
*Aspect*.—Slightly undulate.

Sinuses:

*Shape of petiolar sinus*.—High widened.
*Shape of base petiolar sinus*.—High widened.
*Depth of petiolar sinus*.—5 cm.
*Width of petiolar sinus*.—2.6 cm.
*Shape of upper sinuses*.—High widened.

Color:

*Immature foliage upper side*.—RHS Green 137A.
*Immature foliage under side*.—RHS Green 138B.
*Mature foliage upper side*.—RHS Green 137A.
*Mature foliage under side*.—RHS Green 138B.

Venation:

*Type*.—Pinnate.
*Venation color upper side*.—Near RHS Yellow-Green 154C.
*Venation color under side*.—Near RHS Yellow-Green 154C.

Petiole:

*Length*.—15 cm.
*Diameter*.—0.5 cm.
*Color*.—RHS Yellow-Green 145A, moderately flushed Greyed-Purple 184C.
*Texture*.—Glabrous to very slightly pubescent.

FLOWER

Flowering period begins mid to early May in Bakersfield, Calif.

Inflorescence when in bud:

*Length*.—11 cm.
*Diameter*.—5 cm.
*Bud color*.—Near RHS Green 140B.
*Bud shape*.—Conical.
*Bud size*.—About 1 to 2 mm by 1 to 2 mm.

Individual flower:

*Main time of flowering*.—7 days.
*Size of entire flower* (*to end of stamens*).—0.6 cm.
*Calyx shape*.—Funnel.
*Calyx size*.—1.3 cm.
*Calyx color*.—Near RHS Green 140A.
*Calyx apex*.—Rounded.
*Calyx base*.—Rounded.
*Calyx texture*.—Glabrous all surfaces.
*Diameter*.—15 mm.
*Quantity per flowering stem*.—5.
*Days lasting on plant*.—7 days.

Petals:

*Quantity*.—5.
*Arrangement*.—Symmetrical rotate.
*Length*.—0.19 cm.
*Width*.—<0.1 cm.
*Shape*.—Obovate.
*Apex*.—Ovate.
*Base*.—Ovate.
*Texture, upper and lower surfaces*.—Soft.
*Color*.—At opening upper surface: Near RHS Green 140B. At opening lower surface: Near RHS Green 140B. Fully opened upper Surface: Near RHS Green 140B. Fully opened under Surface: Near RHS Green 140B.

Peduncles:

*Fruit peduncle length*.—45 mm.
*Fruit peduncle width*.—4 mm.
*Angle*.—About 65° to the lateral branch.
*Fruit peduncle strength*.—Medium.

*Fruit peduncle texture.*—Softly pubescent.
*Color.*—Near RHS Green 142D.
Pedicels
*Length.*—0.8 cm.
*Diameter.*—0.05 cm.
*Angle.*—About 70° to center of flower cluster.
*Strength.*—Very strong.
*Texture.*—Softly pubescent.
*Color.*—Near RHS Green 141C.
Fragrance: Absent.

REPRODUCTIVE ORGANS

Number of stamens: 5.
Anthers:
*Shape.*—Oblong.
*Length.*—Approximately 0.1 cm.
*Color.*—Near Yellow 9C.
Pollen:
*Color.*—Near Yellow 8A.
Quantity: Abundant.
Pistil quantity: 1.
*Length.*—0.3 cm.
Style:
*Length.*—<0.1 cm.
*Color.*—Near RHS Green 143B.
Stigma:
*Shape.*—Round.
*Color.*—Near RHS Yellow-Green 144D.
Ovary color: Near RHS Yellow-Green 144D.

FRUIT

Cluster:
*Average length.*—18 to 25 cm.
*Average diameter.*—7 cm.
*Average weight.*—160 to 180 grams.
*Density.*—Dense about 98 berries per cluster.
Fruit (berry):
*Average length.*—15 to 20 mm.
*Average diameter.*—14 to 17 mm.
*Weight.*—About 3 grams.
*Shape.*—Sphere.
*Cross-section.*—Circular.
*Color of berry skin.*—Young Fruit: Near RHS Greyed-Purple187C and 187D. Slight glaucous layer near Purple 76D. Older Fruit: Near RHS Violet-Blue N92B, flushed N92A. Moderate glaucous layer near Violet-Blue 92D.
*Color of berry flesh.*—Near RHS Violet-Blue N92A with sheen of Grey 201B.
*Thickness of skin.*—Medium.
*Flavor description.*—Sweet, full dark grape flavor, uniquely strong flavor which is a mixture of muscat and labrusca, sometimes popularly referred to as "gummy bear flavored".
Seed:
*Presence.*—Infrequent.
*Length.*—2 to 3 mm.
*Width.*—2 mm.
*Harvest time.*—Fruiting period end of June until mid-July in Bakersfield, Calif.

OTHER CHARACTERISTICS

Disease and pest resistance: Not observed to be susceptible nor resistant to normal diseases and pests of *Vitis labrusca.*
Temperature tolerance: Observed growing between 6° C. to 41° C.
Drought tolerance: Drought is tolerated by the plants, but, will significantly reduce the size of the berries.
What is claimed is:
1. A new and distinct cultivar of *Vitis* grapevine plant named 'CXG20' as herein illustrated and described.

* * * * *